United States Patent [19]

Wessling et al.

[11] Patent Number: 4,797,456

[45] Date of Patent: Jan. 10, 1989

[54] AQUEOUS-DISPERSIBLE CYCLIC SULFONIUM COMPOUNDS THAT CURE TO FORM WATER-INSOLUBLE POLYMERS

[75] Inventors: Ritchie A. Wessling; Donald L. Schmidt, both of Midland, Mich.; Kiyoshi I. Aikawa, Chiba Prefecture, Japan

[73] Assignee: The Dow Chemical Company, Midland, Mich.

[21] Appl. No.: 448,083

[22] Filed: Dec. 9, 1982

[51] Int. Cl.[4] .................... C08G 59/14; C08F 128/06; C07D 333/02

[52] U.S. Cl. .................................. 525/531; 525/348; 528/109; 544/59; 549/66; 549/13; 549/28; 549/29; 549/65; 549/74; 549/68; 549/75; 549/76; 549/77; 549/78; 549/79

[58] Field of Search .................. 544/59; 528/109, 360, 528/380; 525/348, 531; 549/13, 23, 28, 30, 46, 65, 66, 68, 69, 74, 75, 76, 77, 78, 79, 80, 83

[56] References Cited

U.S. PATENT DOCUMENTS

| | | | |
|---|---|---|---|
| 3,078,259 | 2/1963 | Hatch | 526/287 |
| 3,130,174 | 4/1964 | Lloyd | 524/3 |
| 3,144,438 | 8/1964 | Sosnovsky . | |
| 3,544,499 | 12/1970 | Hatch | 528/360 |
| 4,020,030 | 4/1977 | Harris . | |
| 4,096,154 | 6/1978 | Rampfler | 549/80 |
| 4,233,421 | 11/1980 | Worm | 525/348 |
| 4,301,044 | 11/1981 | Wentler | 252/545 |
| 4,331,574 | 5/1982 | BeKooij | 525/530 |
| 4,337,185 | 6/1982 | Wessling | 524/458 |

*Primary Examiner*—Christopher Henderson

[57] ABSTRACT

Water-soluble sulfonium salts are converted, without the elimination of odorous volatile by-products, to water-insoluble products useful as binders in coating formulations by heating a water-soluble cyclic sulfonium salt in which the sulfonium sulfur is bonded only to aliphatic carbons.

3 Claims, No Drawings

AQUEOUS-DISPERSIBLE CYCLIC SULFONIUM COMPOUNDS THAT CURE TO FORM WATER-INSOLUBLE POLYMERS

BACKGROUND OF THE INVENTION

This invention relates to inherently water-dispersible compounds which cure upon exposure to heat and to the use of such compounds to produce water-insoluble materials.

Most coating and other product formulations are employed in a fluidized state and are then dried or cured to solid continuous films or articles that are water-resistant. The films are also adherent to the substrate to which they are applied. Thus such fluid formulations usually contain a vehicle and miscellaneous ingredients such as pigments, extenders, fungicides and the like. The vehicle is a fluid consisting of a solution or a mixture of a binder with a thinner or solvent. The binder is the primary constituent since it binds itself and any optional ingredients to the substrate or urface of the object being coated. See, for example, Bobalek and Fisher, *Organic Protective Coatings*, Reinhold, (1953); and Martens, *Emulsion and Water-Soluble Paints and Coatings*, Reinhold, (1964). To enable the coatings to dry or cure to form continuous adhesive films, binders that are polymeric or polymerize after application to the substrate have generally been employed. In order that the coatings have a desired water resistance, the binders used are generally hydrophobic and are therefore, not soluble in water. Thus, the liquid thinner or solvent usually required to fluidize the binder, has generally been an organic solvent such as xylene, toluene, various alcohols and the like. Such solvents are generally more expensive than water and are often toxic or flammable, thus requiring expensive precautions when coating formulations containing them are stored and used.

In view of the foregoing disadvantages of such organic solvents or thinners, it is highly desirable to employ a binder which can be dissolved or thinned by water and yet will produce a water-resistant film when applied to a substrate and then dried or cured. While coating formulations having latex binders wherein the hydrophobic binder is colloidally dispersed in an aqueous dispersing medium are used widely in the coating industries, such coatings suffer from various shortcomings. For example, the flow properties are often not as satisfactory as those wherein the binder is dissolved in an organic liquid. Also undesirable coagulation of the latex can occur when the formulation is exposed to low temperatures. Also well-known, the water-borne synthetic resinous binders such as amino-functionalized epoxies and carboxylated acrylates have the disadvantage of significant water sensitivity and require high curing temperatures and cross-linking agents such as amine/aldehyde condensates and blocked polyisocyanates.

In view of these problems with the aforementioned water-dispersible and water-soluble binders, recent attempts have been made to prepare coating formulations containing water-soluble binders which convert to highly water-resistant coatings upon curing. Examples of such product formulations are described in U.S. Pat. Nos. 3,544,499 and 4,020,030. Unfortunately, however, while the sulfonium-containing binders described in the aforementioned references cure to form highly water-resistant materials, they generally evolve an undesirable odorous vapor during the curing process.

In view of the deficiencies of the prior art product formulations, it is now highly desirable to provide a water-soluble binder material which cures to a highly water-resistant material without evolving an odorous vapor.

SUMMARY OF THE INVENTION

The present invention is such an aqueous-dispersible cyclic sulfonium salt represented by the formula

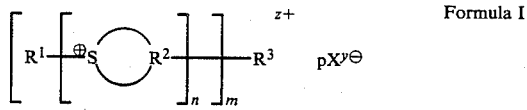

Formula I wherein $R^1$ is an n-valent organic radical wherein each valence bond to the sulfonium moiety is on an aliphatic carbon; $R^2$ is a divalent organic radical that unites with the sulfonium atom to form a 5- to 7-membered ring; said divalent radical bearing a molecular weight enhancing m-valent substituent ($R^3$); X is a suitable counteranion; n is an integer from 1 to 500; m is an integer from 1 to 500 provided that the product of m and n is equal to or less than 500; y is a number from 1 to 4; z is a number corresponding to the net cationic charge on the sulfonium cation; and p is a number equal to z/y. Alternatively, the counteranion, X, is covalently bonded to $R^1$, $R^2$, or $R^3$ of the sulfonium cation in which case, the salt is a zwitterion or inner salt represented by the formula:

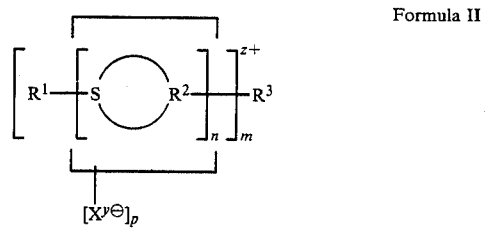

Formula II wherein $R^1$, $R^2$, $R^3$, X, m, n, p, y and z are as defined before except that $R^1$, $R^2$ and/or $R^3$ become polyvalent in order to covalently bond with X. This salt is capable of being converted to a water-insoluble product by conversion of the cyclic sulfonium moiety to a sulfide moiety without the elimination of volatile, sulfur-containing by-products. For purposes of this invention an aqueous dispersible compound means that (1) the compound spontaneously forms a thermodynamically stable mixture with an aqueous medium including true solutions wherein individual molecules of the compound are dispersed as well as colloidal (micellular) solutions wherein the molecules are aggregated to some extent, or (2) the compound can be dispersed in an aqueous medium without the aid of a surfactant to form a synthetic latex which is meta-stable in the thermodynamic sense. By an aqueous medium is meant water or a solution of a water-miscible polar liquid such as an alcohol or a cyclic ether in water.

In another aspect, this invention is a binder formulation wherein at least a portion of the binder constituent thereof is the aforementioned sulfonium salt. Further aspects of this invention are (1) a solid, continuous, water-insoluble binder that results from thermally curing the aforementioned sulfonium salt and (2) substrates coated with said binder or coating.

Surprisingly, the binder formulations of the present invention cure on exposure to heat to form highly water-resistant coatings or other materials having excellent physical properties such as adhesion, abrasion resistance and color without evolving observable amounts of undesirable sulfide odors. The sulfonium compounds of the present invention are usefully employed as the binder components in such coating formulations such as paints, lacquers, paper coatings and flooring materials; as well as binder components of adhesives, fiber-reinforced plastics and encapsulants.

Detailed Description of Preferred Embodiments

The sulfonium salt (binder) employed in the present invention as represented by Formula I stated hereinbefore, contains at least one 5- to 7-membered cyclic sulfonium moiety. The cyclic sulfonium moiety bears a molecular weight enhancing m-valent substituent ($R^3$). By "molecular weight enhancing" substituent is meant a substituent which, as a result of its containing (1) chemically active groups capable of coupling with a nonvolatile compound and/or (2) a group of sufficient molecular weight, is or can readily become nonvolatile. Preferably, this substituent contains an addition polymerizable, ethylenically unsaturated group, a functional group that is capable of coupling with a nonvolatile organic compound, and/or a group of sufficient molecular weight to render the sulfonium salt and its reaction products nonvolatile under conditions required to cure the sulfonium salt to a water-insoluble solid. This cyclic sulfonium salt contains a sufficient concentration of the cyclic sulfonium moieties to render the salt water-soluble. By "water-soluble" is meant that at least one, preferably from about 25 to about 400, weight parts of the sulfonium salt will spontaneously disperse in 100 weight parts of water to form a thermodynamically stable mixture with the water. These thermodynamically stable mixtures form spontaneously and include true solutions wherein the individual sulfonium compound molecules are dispersed as well as micellular or colloidal solutions wherein the sulfonium salts are aggregated to some extent. The cyclic sulfonium moiety reacts with a nucleophilic anion under the curing conditions to form a nonvolatile, water-insoluble sulfide moiety. This sulfide moiety can be formed either (1) by cleaving the bond between $R^1$ and the sulfur atom wherein $R^1$ is eliminated or, preferably, (2) by a ring-opening reaction in which one of the bonds between the sulfur and $R^2$ are broken wherein no potentially volatile product is eliminated. It is further required that at least one of $R^1$ and $R^3$ are groups that provide the sulfonium salt with a binder capability. By "binder capability" is meant that the group is a polymeric binder or is polymerizable to form a polymer that can act as a suitable binder upon drying and thermal curing.

Illustratively, $R^1$ is an n-valent organic radical that can be suitably bonded to a sulfonium moiety. Preferably, $R^1$ radicals include residues of epoxy resins that bear at least 1, and preferably a plurality of pendant or terminal oxirane moieties (often called vicinal epoxy groups), residues of polymers of glycidyl acrylates, methacrylates, haloacrylates and halomethacrylates; styryl oxiranes, styryl glycidyl ethers, allylglycidyl ethers; and other resinous epoxy-containing reactants as described in U.S. Pat. No. 4,020,030. Suitable, but less preferred, $R^1$ radicals include residues of polymers and copolymers of vinylbenzyl halides such as vinylbenzyl chloride and vinylbenzyl bromide, chloromethyl butadiene, isopropenyl benzylhalides, and the like. Of the foregoing residues, the residues of the epoxy resins are preferred, with those being described in U.S. Pat. No. 4,020,030 being especially preferred.

Representative of $R^2$ moieties are trivalent organic radicals which bond to the sulfonium atom to form 5- to 7-membered heterocyclic rings. While two of the valence bonds of $R^2$ are linked to the sulfonium atom, the remaining valence bond is linked to $R^3$. Preferably, $R^2$ combines with the sulfonium atom to form a 5- or 6-membered ring, with the 5-membered rings being especially preferred. While $R^2$ is advantageously hydrocarbon such as alkanetriyl, $R^2$ is suitably a trivalent heterohydrocarbon radical wherein the chain of the hydrocarbon is interrupted by a hetero atom, for example, oxygen, nitrogen or sulfur. In all suitable $R^2$ moieties, the two carbons of $R^2$ bonded to the sulfonium atom are methylene. Exemplary suitable hydrocarbanetriyls and trivalent heterohydrocarbons include alkanetriyl, cycloalkanetriyl, alkenetriyl, a trivalent alkanearylalkane, a trivalent alkylarylalkyl, a trivalent alkyloxyalkyl, a trivalent alkylaminoalkyl and a trivalent alkylthioalkyl. In addition to $R^3$, it is understood that $R^2$ may bear additional substituents in positions that are nonadjacent to the sulfonium atom. Such additional substituents may be hydroxyl, alkyl, alkoxy, and thioalkyl. Most preferably, $R^2$ is 1,2,4-butanetriyl.

When $R^3$ contains an addition polymerizable ethylenically unsaturated group, representative $R^3$ moieties include $\alpha,\beta$-alkenylcarbonyloxy moieties such as acryloyl and methacryloyloxy; $\alpha,\beta$-alkenyl carbonyl, such as acryloyl; vinylhydrocarbyloxy moieties, such as vinylbenzyloxy including substituted vinylbenzyloxy, and allyloxy; $\alpha,\beta$-alkenyl amides such as acrylamido; alkenyloxy carbonyl such as vinyloxy carbonyl; $\alpha,\beta$-alkenylamino carbonyl, such as vinylcarbamato; $\alpha,\beta$-alkenyl carbonyloxyalkylamino; carbonyloxy such as acryloylethylaminocarbonyloxy; and maleate half esters.

When $R^3$ contains a chemically active functional group, representative $R^3$ moieties include hydroxyl, hydroxyalkyl, hydroxyaryl, amino, aminoalkyl, carboxyl, blocked isocyanate, such as toluene diisocyanate which is sequentially reacted with 2-ethylhexanol and hydroxythiophane and sulfhydryl.

When $R^3$ is a nonvolatile group, representative $R^3$ moieties include hydrocarbyl carbonyloxy having a molecular weight greater than 300 such as dimerized linseed acids, functionally terminated oligomers of vinyl monomers wherein the functional groups are hydroxy, amino, carboxylic acid and the like, such as styrene and butadiene wherein the oligomer has a molecular weight greater than 500; and similar high molecular weight moieties.

Of the foregoing $R^3$ moieties, acryloyloxy, methacryloyloxy, acryloyl methacryloyl and alkoxymaleoyloxy are preferred, with acryloyloxy and methacryloyloxy being especially preferred.

$X^{y\ominus}$ is an anion, for example, hydroxide; saturated carboxylates such as acetate, formate or lactate; unsaturated carboxylates such as acrylate and maleate; polycarboxylates such as phthalate, trimesate, pyromellitate, polyacrylate, citrate, tartarate and others as specified hereinafter; bicarbonate; sulfate; dihydrogenphosphate; alkylaryl, sulfonates such as benzene sulfonate; or another suitably inert anion which forms an aqueous-dispersible salt with the sulfonium cation. Of the foregoing, the aforementioned carboxylates are preferred, with the saturated carboxylates such as lactate and unsaturated carboxylates such as acrylate being especially preferred.

In the foregoing formula, n is a whole number from 1 to 500, m is a whole number from 1 to 500 provided that m×n<500, y corresponds to the valence of X and p is equal to n times m divided by y. Preferably, m is equal to 1 and n is equal to 2 and y is 2 to 4.

Exemplary preferred sulfonium salts are represented by the following formula:

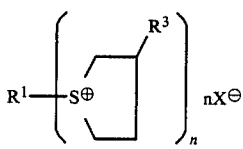

Formula III wherein $R^1$ is alkyl, hydroxyalkyl or residue of an epoxy resin which has been reacted with a sulfide to form a sulfonium moiety; $R^3$ is hydroxyl, acryloyloxy, oxymaleoyloxalate or methacryloyloxy; X is lactate or acrylate and n is 1 to 4.

The aforementioned sulfonium salts wherein $R^3$ is hydroxyl are prepared by reacting hydroxythiophane with an alkylating agent such as an epoxy compound or alkyl halide or arylalkyl halide. Preferably, the hydroxythiophane is reacted with an epoxy resin having terminal oxirane groups according to the procedure and conditions described in U.S. Pat. No. 4,020,030 using an epoxy resin as exemplified therein to form the sulfonium salt. When it is desirable that the anion (X) be other than that generated in the sulfonium-forming reaction, the undesirable anion is readily exchanged by conventional means, e.g., ion-exchange resins, to the desired anion, e.g., bicarbonate or hydroxide. The resulting salt solution can then be neutralized with any suitable acid to form other desired anions.

In the preparation of the sulfonium compounds wherein $R^3$ is acryloyl or similar moiety, the sulfonium compound is prepared by first reacting the hydroxythiophane with acrylic acid, acrylic anhydride, acryloyl chloride or similar acid, anhydride or acid chloride to form a desired ester of the hydroxythiophane. Alternatively, this desired ester may be formed by a transesterification reaction, e.g., by contacting the hydroxythiophane with methyl acrylate.

The acryloyloxythiophane or similar thiophane ester of an unsaturated acid can be alkylated using conventional alkylating agents as described above and conditions as described in U.S. Pat. No. 4,337,185 to form a sulfonium salt represented by the formula:

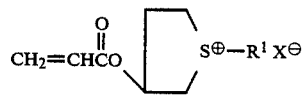

wherein $R^1$ and $X^\ominus$ are as defined hereinbefore, most preferably $R^1$ is 2-hydroxypropyl and $X^\ominus$ is 2-hydroxypropionate. This monomeric salt is water-soluble and can be homopolymerized or copolymerized with other water-soluble monomers such as acrylamide, acrylic acid and the like using aqueous solution polymerization to form water-soluble polyelectrolytes. Alternatively, this monomeric salt may be copolymerized with water-insoluble monomers such as styrene, butadiene, methyl methacrylate, ethyl acrylate or other emulsion polymerizable monomers using emulsion polymerization conditions to form cationic latexes which are useful in coating applications.

Alternatively, the acryloyloxythiophane or similar thiophane ester of an unsaturated acid may be polymerized or copolymerized to form a polymer having pendant thiophane moieties. Alkylation of these moieties with, for example, propylene oxide and lactic acid yields a water-dispersible or water-soluble polyelectrolyte having pendant aliphatic cyclic sulfonium moieties. When this polyelectrolyte is heated to dryness, it decomposes to form a nonionic product without releasing volatile sulfides.

Also, the acryloyloxythiophanes or other similar thiophane ester monomers can be converted to water-soluble thermosetting monomers by reacting such esters with an ethylenically unsaturated alkylating agent, e.g., glycidyl methacrylate, styryl glycidyl ether or allyl glycidyl ether, and with an ethylenically unsaturated acid such as acrylic, methacrylic, 3-acrylamido-2-methyl propane sulfonic (AMPS), maleic or itaconic acid, to form a salt, an example of which is represented by the formula:

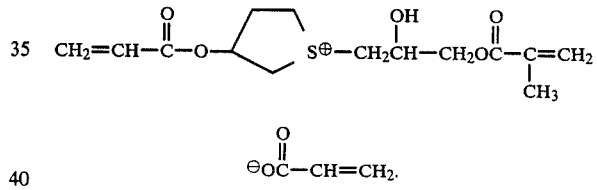

These thermosetting salts are very water-soluble and yield low viscosity aqueous solutions, e.g., an aqueous solution of 20 weight percent of the above salt will exhibit a Brookfield viscosity (LVT Viscometer, No. 3 spindle, 30 rpm at 25° C.) less than 5,000 centipoise. When formulation with photoinitiators such as dithiocarbonates, dithiocarbamates or others described in U.S. Pat. No. 4,233,425, aqueous solutions of such thermosetting salts are curable using radiation. Accordingly, they may be cured in the form of coating inks and similar formulations without producing volatile by-products.

A polyethylenic zwitterion form of the monomeric sulfonium salt may be prepared by reacting hydroxythiophane with maleic anhydride or similar ethylenically unsaturated polyacid monomer to form the thiophane ester of the polyacid monomer. This ester is then alkylated with an ethylenically unsaturated alkylating agent such as glycidyl methacrylate to form, for example, a zwitterion represented by the formula:

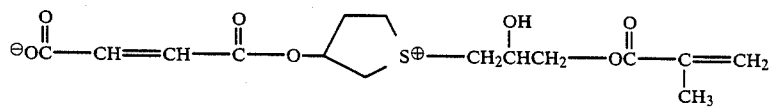

This monomer is a thermosetting one similar to the aforementioned thermosetting monomer salt except that this monomer is somewhat less reactive.

Monomeric salts similar to the aforementioned ones derived from hydroxythiophane can be prepared by substituting thiomorpholine for the hydroxythiophane and using amidation instead of an esterification to form salts having the formula:

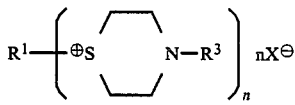

wherein $R^1$, $R^3$, n and $X^\ominus$ are as defined hereinbefore. An example of such a salt is represented by the formula:

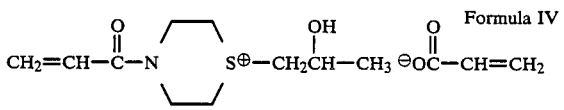

Formula IV which is formed by first reacting acryloyl chloride, acrylic anhydride or methyl acrylate with this morpholine using conventional amidation conditions and then alkylating the resulting amide using propylene oxide and acrylic acid to form the desired sulfonium acrylate salt. Other amide salts of similar aforementioned thiophane to the ester salts may be prepared by procedures similar to those described above.

Polymers of the aforementioned sulfonium salts are useful as binders in coating applications. They are normally applied as an aqueous solution or an aqueous dispersion, e.g., a latex, thereof to the substrate and subsequently thermally cured or in some instances cured via radiation and heat. Convenient cure rates have been observed at temperatures of from about 60° C. to about 180° C., but higher or lower temperatures could be used at the convenience of the user. Normally such curing occurs at a temperature above the second order transition temperature ($T_g$) of the polymerized salt. Alternatively, polymers of the sulfonium salts can be partially cured (B-stage) to a glassy state after removal of water and subsequently cured to completion by heating the partially cured polymer to a temperature above the $T_g$ of the fully cured product.

While these sulfonium salts can be employed as the sole binder component in coating formulations, it is sometimes desirable to use them in combination with water-compatible, thermally-curable resins which will react with the hydroxy groups on the sulfonium salts which have been prepared by reacting an oxirane compound (epoxy resins) with a cyclic sulfide. Thus more extensive cross-linking may be achieved. Bronsted acids also catalyze this cross-linking reaction. Suitable water-compatible, thermally-curable resins include urea/formaldehyde resins, imino urea/formaldehyde resins, melamine/formaldehyde resins, phenol/formaldehyde resins and the like. Such resins are normally used in amounts of from about 5 to about 50 weight percent based on the weight of the sulfonium compound, and are preferably used in amounts from about 10 to about 30 weight percent. Alternatively, such resins may be blocked isocyanates containing tin catalysts as taught in EPO Application No. 14851 published Sept. 3, 1980. Other cross-linking agents can also be used in addition to or as substitutes for such water-compatible, thermally-curable resins. For example, a polycarboxylic acid can be employed as the anion of the sulfonium compound, thereby forming a polyanion which is an inherent cross-linking agent at temperatures sufficient to remove water from the coating formulations. Examples of suitable polycarboxylic acids include oxalic, malonic, maleic, succinic, adipic, citric, itaconic, isophthalic, terephthalic, trimesic polyacrylic and polymethacrylic acids, copolymers of acrylic and/or methacrylic acids with ($C_1$ to $C_4$) alkyl acrylates and/or methacrylates, carboxylated polybutadiene and the like. The reaction of polycarboxylic acids (or polycarboxylates) with the cyclic sulfonium groups give extended and/or cross-linked ring-opened products having sulfide and ester linkages. Such extended and/or cross-linked products are novel compositions. Conversely, the sulfonium salts can be used as cross-linking agents for water-compatible carboxyl-containing polymers in a similar manner. Other conventional additives can likewise be included in the instant coating compositions, such as leveling agents, pigments, fillers, cosolvents, foam control agents, etc.

The following examples are set forth to illustrate the invention and should not be construed as limiting its scope. Unless otherwise indicated all parts and percentages are by weight.

EXAMPLE 1

A. Preparation of 3-Hydroxythiophane

Into a two-liter reaction vessel containing 500 ml of a suspension of finely divided aluminum chloride (1.05 moles) in methylene chloride which is maintained between −10° C. and −20° C. is added 1 mole of chloroacetylchloride. Dry ethylene is then passed through the resulting solution while stirring and maintaining the temperature below 10° C. Absorption of the ethylene is rapid and ceases when a stoichiometric amount has been absorbed in approximately 3 hours under normal pressure. While continuing to maintain the temperature of the reaction mixture below 5° C, 110 ml of water is introduced dropwise into the reaction mixture thereby generating hydrogen chloride which is passed over 5 N NaOH solution. The reaction mixture is stirred vigorously for an additional hour after strong hydrogen chloride evolution has terminated. The reaction mixture is then filtered and the organic layer is withdrawn and vacuum distilled to provide an 80 percent yield of 1,4-dichloro-2-butanone.

One mole of the aforementioned butanone in 100 ml of methanol is contacted with 0.25 mole of aqueous sodium borohydride. The resulting mixture is extracted with methylene chloride and vacuum distilled to provide an 84 percent yield of 1,4-dichloro-2-butanol. This resulting 1,4-dichloro-2-butanol (1 mole) is added slowly over a period of 90 minutes to 586.2 g of an aqueous solution containing 1.1 moles $Na_2S$ 9 $H_2O$ at 70° C. under vigorous agitation. After the addition is complete, the mixture is held for an additional 60 minutes at 70° C., and a major portion of the methanol is reoved by distillation. The resulting product is extracted with three 80-ml portions of methylene chloride and then vacuum distilled to provide 3-hydroxythiophane.

B. Preparation of 3-Maleoxyacidthiophane

A solution of 0.2 mole of 3-hydroxythiophane and 0.2 mole of maleic anhydride in 30 ml of 1,2-dichlorethane is heated to 80° C. with stirring for 4 hours in the presence of 1 mole percent of 4-dimethylaminopyridine. The resulting 3-maleoxyacidthiophane is recovered by washing the aforementioned reaction product with two 50-ml portions of water, separating the oil layer and distilling the oil layer under vacuum.

C. Preparation of 3-Methacryloyloxythiophane

3-Methacryloyloxythiophane is prepared by dissolving 0.2 mole of 3-hydroxythiophane in 30 ml of dry methylene chloride and reacting it with a slight excess (0.21 mole) of methacryloyl chloride at 47° C. and vigorous stirring for 6 hours. Hydrogen chloride evolved during the reaction is passed through a caustic solution. A 0.05 mole portion of potassium carbonate is introduced into the reaction mixture as an acid scavenger, and the reaction is maintained for an additional hour at 47° C. The reaction mixture is washed with two 50-ml portions of water. The resulting oil layer is removed and vacuum distilled to provide the desired 3-methacryloyloxythiophane.

D. Conversion of Ester to Sulfonium Salt and Coating Application

The ester is converted to the sulfonium form of the 3-maleoxyacidthiophane (ester) by dispersing 20.2 g of the ester in 10 g of water and heating the dispersion to 70° C. while vigorously agitating the dispersion. A stoichiometric amount of an epoxy novolac resin having a functionality of ~3.5 and an epoxide equivalent weight of 175-182, containing 15 percent of acetone dispersed in a mixture of 10 g of acetone and 10 g of water is added with stirring to the aforementioned ester. The resulting mixture is held at 70° C. under vigorous agitation for 30 minutes until a clear solution is obtained. Acetone is then removed by volatilization, and the concentration of water is adjusted to 35 percent. The resulting aqueous solution of sulfonium salt, represented by the formula:

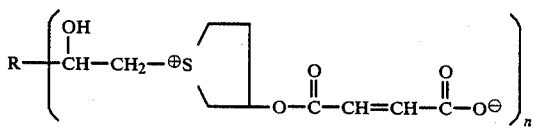

wherein R is the residue of the epoxy resin and n is 3.5 is then applied as a coating to an aluminum substrate using a Meyer rod. The resulting coating is then cured by heating to 175° C. for 5 minutes. The cured coating is submerged in boiling water for 30 minutes without exhibiting any delamination from the substrate or loss of clarity.

EXAMPLE 2

A 17.2-g portion of 3-methacryloyloxythiophane as prepared in Example 1 and 5.8 g of fumaric acid are dispersed in 10 g of a 50:50 mixture of water and isopropanol and then heated to 75° C. To this dispersion is added 17.5 g of bisphenol A diglycidyl ether slowly while vigorously agitating the dispersion. To the resulting mixture is added 0.4 g of t-butyl perbenzoate. The resulting mixture is applied to a fiber glass cloth to saturate it such that after drying, the resulting laminate contains 30 weight percent of resin. The resulting laminate is cured at 160° C. for 5 minutes to produce a cured laminate having physical properties equal to or better than laminates produced from conventional epoxy resins and curing agents. No odorous volatile by-products are observed during the curing process.

What is claimed is:

1. A water-soluble cyclic aliphatic sulfonium salt represented by the formulas:

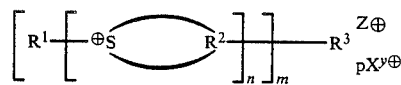

or

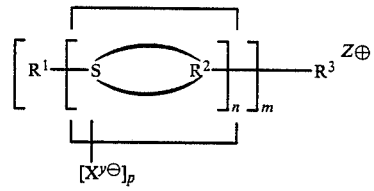

wherein $R^1$ is a n-valent organic radical wherein each valence bond to the sulfonium moiety is on an aliphatic carbon other than benzyl; $R^2$ is a polyvalent organic radical that unites with the sulfonium atom to form a 5- to 7-membered ring, said $R^2$ bearing a molecular weight enhancing substituent ($R^3$); $R^3$ is an $\alpha,\beta$-alkenyl carbonyloxy moiety and X is a hydroxide, saturated carboxylate, polycarboxylate, bicarbonate, sulfate or alkylaryl sulfonate; n is an integer from 1 to 500, m is an integer from 1 to 500 provided that the produce of $m \times n \geq 500$, y is a number from 1 to 4, z is a number corresponding to the net cationic charge on the sulfonium cation and p is a number equal to z/y.

2. A water-soluble cyclic aliphatic sulfonium salt represented by the formula:

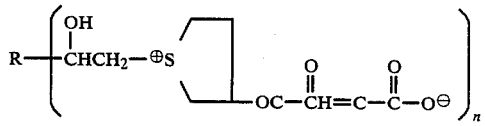

wherein R is the residue of an epoxy resin and n is 3.5.

3. A water-soluble cyclic aliphatic sulfonium salt which is the reaction produce ot 3-methacryloyloxythiophane, fumaric acid and bisphenol A diglycidyl ether.

* * * * *